(12) United States Patent
Vital et al.

(10) Patent No.: US 11,065,164 B1
(45) Date of Patent: Jul. 20, 2021

(54) SMART BANDAGE FOR ELECTROCHEMICAL MONITORING AND SENSING USING FABRIC-INTEGRATED DATA MODULATION

(71) Applicants: Dieff Vital, Miami, FL (US); Shubhendu Bhardwaj, Miami, FL (US); John L. Volakis, Miami, FL (US); Pulak Bhushan, Miami, FL (US); Shekhar Bhansali, Weston, FL (US)

(72) Inventors: Dieff Vital, Miami, FL (US); Shubhendu Bhardwaj, Miami, FL (US); John L. Volakis, Miami, FL (US); Pulak Bhushan, Miami, FL (US); Shekhar Bhansali, Weston, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 17/157,624

(22) Filed: Jan. 25, 2021

(51) Int. Cl.
  *A61B 5/145* (2006.01)
  *A61F 13/84* (2006.01)
  *A61B 5/1486* (2006.01)
  *A61B 5/00* (2006.01)
  *A61B 5/01* (2006.01)
  (Continued)

(52) U.S. Cl.
  CPC .......... *A61F 13/84* (2013.01); *A61B 5/01* (2013.01); *A61B 5/1486* (2013.01); *A61B 5/14539* (2013.01); *A61B 5/14542* (2013.01); *A61B 5/14546* (2013.01); *A61B 5/445* (2013.01); *A61B 5/4875* (2013.01); *A61B 5/742* (2013.01);
  (Continued)

(58) Field of Classification Search
  CPC ............... A61F 13/84; A61F 2013/424; A61F 2013/8473; A61F 2013/8479; A61B 5/01; A61B 5/14539; A61B 5/14542; A61B 5/14546; A61B 5/1486; A61B 5/445; A61B 5/4875; A61B 5/7405; A61B 5/742; A61B 5/7455; A61B 10/0045; A61B 5/0008; H04B 7/26
  See application file for complete search history.

(56) References Cited

U.S. PATENT DOCUMENTS

| 2018/0055359 A1* | 3/2018 | Shamim | A61B 5/14539 |
| 2020/0178801 A1* | 6/2020 | Nazari | A61B 5/0031 |
| 2020/0297255 A1* | 9/2020 | Martinez | A61B 5/447 |

OTHER PUBLICATIONS

Pal, et al., "Early detection and monitoring of chronic wounds using low-cost omniphobic paper-based smart bandages," Biosensors and Bioelectronics, vol. 117, 2018, pp. 696-705 (Year: 2018).*

(Continued)

*Primary Examiner* — Eric J Messersmith
(74) *Attorney, Agent, or Firm* — Saliwanchik, Lloyd & Eisenschenk

(57) ABSTRACT

Systems and methods for a low-cost smart textile electronic (tex-tronic) useful for wound healing assessment are provided. Data collection can be accomplished by reflection of the modulated wound-data to an interrogator. The RF modulation of the data can be done by a textile-based voltage-controlled oscillator (VCO) that takes the electric signal provided by electrochemical sensing of the uric acid found in the wound fluid. The low-cost smart textile electronic uses low-cost materials and is easy to manufacture and use by any patient or medical professional.

20 Claims, 10 Drawing Sheets

(51) Int. Cl.
  *A61B 10/00* (2006.01)
  *H04B 7/26* (2006.01)
  *A61F 13/42* (2006.01)

(52) U.S. Cl.
  CPC .......... *A61B 5/7405* (2013.01); *A61B 5/7455* (2013.01); *A61B 10/0045* (2013.01); *A61B 5/0008* (2013.01); *A61F 2013/424* (2013.01); *A61F 2013/8473* (2013.01); *A61F 2013/8479* (2013.01); *H04B 7/26* (2013.01)

(56) References Cited

OTHER PUBLICATIONS

Kassal et al., "Smart bandage with wireless connectivity for uric acid biosensing as an indicator of wound status," Electrochemistry Communications, vol. 56, 2015, pp. 6-10 (Year: 2015).*

Liu, et al., Embroidered electrochemical sensors on gauze for rapid quantification of wound biomarkers, Biosensors and Bioelectronics, vol. 98, 2017, pp. 189-194 (Year: 2017).*

T. Songkakul et al., "Towards a Long-Term Multi-Site Electrochemical Wound Monitoring System," 2019 IEEE Sensors, Montreal, QC, Canada, 2019, pp. 1-4 (Year: 2019).*

Sharifuzzaman, et al., "Smart bandage with integrated multifunctional sensors based on MXene-functionalized porous graphene scaffold for chronic wound care management," Biosensors and Bioelectronics, vol. 169, 2020,112637 (Year: 2020).*

Aniket Pal et al., Early detection and monitoring of chronic wounds using low-cost, omniphobic paper-based smart bandages, Biosensors and Bielectrnics 117 (2018) 696-705.

Petar Kassal et al., Smart bandage with wireless connectivity for uric acid biosensing as an indicator of wound status, Electrochemistry Communications 56 (2015) 6-10.

* cited by examiner

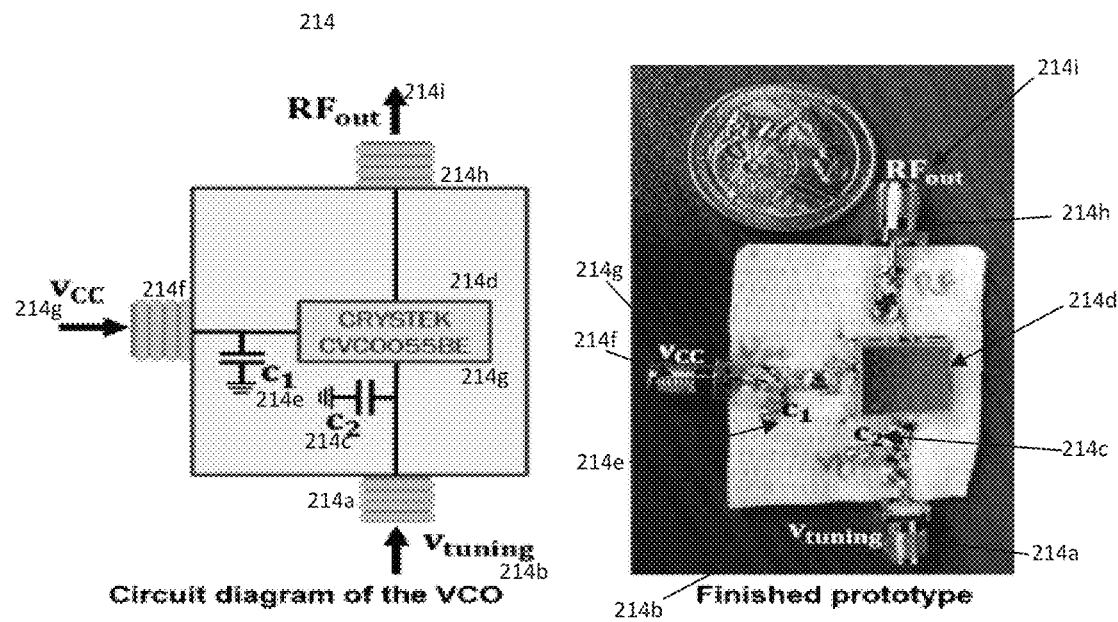
FIG. 4a      FIG. 4b
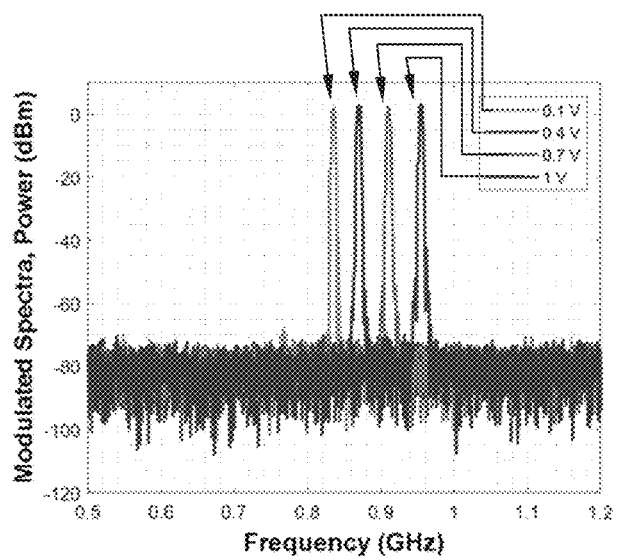
FIG. 5

SMART BANDAGE FOR ELECTROCHEMICAL MONITORING AND SENSING USING FABRIC-INTEGRATED DATA MODULATION

GOVERNMENT SUPPORT

This invention was made with government support under 1160483 awarded by National Science Foundation. The government has certain rights in the invention.

BACKGROUND

Chronic wounds involve a variety of complications starting from difficult or lengthy healing process, high cost of wound care, long-term immobility, infection due to poor wound management, and hospitalization. Effective care for chronic wounds has drawn a lot of attention in recent years. For primary and secondary diagnoses, between $32 and $97 billion are spent annually on wound care according to Nussbaum, et. al., 2018, Value in Health, vol. 21, no. 1, pp. 27-32. Much of this cost may be optimized by using electronic data-collection and wound analytics. Smart electronic monitoring also improves quality of life for the patients, by saving trips to hospitals, providing immediate feedback, and reducing anxiety throughout the healing process. Serious attention should be paid to such a critical health condition as the major consequences can be amputation or death. As the 7th leading cause of death in the US, chronic wounds sound the medical alarm and urge wound researchers to find a better way to help patients who are dealing with wounds to heal faster based on some extra precautions that can be taken and the alleviation of healthcare cost. The latter is often the most concerning factor because most people affected by chronic wounds are from underserved communities. Adaptive therapeutics can yield healing improvement, better quality of life, and healthcare cost reduction.

BRIEF SUMMARY

Certain embodiments of the subject invention provide a low-cost smart textile electronic (tex-tronic, or textronic) for wound healing assessment. This assessment is done by reflection of the modulated wound-data to an interrogator. The RF modulation of the data can then be done by a textile-based voltage-controlled oscillator (VCO) that takes the electric signal provided by electrochemical sensing of, e.g., the uric acid found in the wound fluid. The assessment in some embodiments is based on a threshold of 0.4 mM, with respect to which the severity or restoration of the damaged wound may be evaluated. The average sensitivity of certain exemplary tested embodiments of this system can be in a range of, for example, from 30 to 70 megahertz per millimolar (MHz/mM) (e.g., 44.67 MHz/mM or about 44.67 MHz/mM, and the maximum power consumption can be in a range of, for example, from 0.20 to 0.5 milliwatts (mW) (e.g., 0.38 mW or about 0.38 mW). The subject invention may use low-cost materials and is easy to manufacture and use by any patient, caregiver, or medical professional.

Embodiments of the subject invention may facilitate or allow healing assessment with no or reduced need for removal of bandages or dressings. Some embodiments of the subject invention will assess the healing process of the wound by electrochemical sensing of biomarkers, e.g., uric acid, present in the wound fluid. Uric acid has been reported (by Fernandez, et. al., 2012 International wound journal, vol. 9, no. 2, pp. 139-149; and Umasankar, et. al., 2018, IEEE SENSORS. IEEE, pp. 1-4) to be an excellent biomarker for wound severity based on its concentration. In contrast to existing solutions where complex circuitry is often used for data transfer and processing, certain embodiments of the present invention provide simple, reliable, energy efficient, and cost effective low power systems for wound monitoring.

Certain embodiments of the subject invention provide a smart electronic system based on all-textile minimal circuits for remote sensing and monitoring of wound healing. This system uses an on-fabric voltage-controlled oscillator (VCO) to modulate the wound health-data given by an electrochemical sensor. Some embodiments provide remote sensing and monitoring of both acute and chronic wounds using this system. Certain exemplary embodiments provide a system for wound assessment comprising an electrochemical sensor, a textile-based VCO, and a pair of patch antennas for data transfer, followed by the RF transfer of data from a uric acid sensor integrated with the VCO under practical levels of uric acid emulating the wound fluid.

In an embodiment, an electronic system for remote sensing and monitoring of wound healing in a wound having an associated wound fluid can comprise: a first textile antenna configured to receive an RF power signal; a fabric integrated rectifying circuit configured to convert the RF power signal to a rectified DC supply voltage, the electronic system being configured to operate normally without a power source (i.e., without being physically connected to a power source); a textile based electrochemical sensor configured to receive power from the rectified DC supply voltage and output an electric signal in response to one or more wound health data values of the associated wound fluid; a textile based voltage controlled oscillator (VCO) configured to receive power from the rectified DC supply voltage and modulate the electric signal output by the textile based electrochemical sensor into an RF frequency signal; and a second textile antenna configured to transmit the RF frequency signal modulated by the textile based VCO. The textile based electrochemical sensor can be an enzymatic biosensor configured to monitor levels of uric acid (UA) in the associated wound fluid with a working electrode (WE), a counter electrode (CE), and a reference electrode (RE). The WE and the RE can be used to power the enzymatic biosensor with a sensor potential of from −0.1 V to −2.0 V, such as −0.3 V to −0.9 V (e.g., −0.6 V) from the fabric integrated rectifying circuit. The WE and the CE can be connected to a sensor output resistor having a resistance value of from 100 kΩ to 1000 kΩ, such as 200 kΩ to 500 kΩ (e.g., about 350 kΩ), and the textile based VCO can be configured to read the DC voltage across the sensor output resistor. The system can include an interrogator or a back-end system, or both; and the interrogator can be configured to supply the RF power signal, receive the RF frequency signal, and relay the RF frequency signal to the back-end system for processing and data analysis. The textile based VCO can be configured to receive an input voltage in a range of from 0 V to 10 V, such as 0 V to 6 V, and to provide an output frequency modulation at an output frequency of from 500 MHz to 5000 MHz, such as 830 MHz to 1700 MHz. The textile based electrochemical sensor and the textile based VCO can each be configured to receive power primarily, substantially, or only from the RF power signal, either through the fabric integrated rectifying circuit, through another fabric integrated circuit, or through an external source, method, or circuit.

In an embodiment, a method of monitoring wound health can include providing an electronic system for remote sensing and monitoring of wound healing in a wound having an associated wound fluid, the electronic system including a first textile antenna configured to receive an RF power signal; a fabric integrated rectifying circuit configured to convert the RF power signal to a rectified DC supply voltage, the electronic system being configured to operate normally without a power source (i.e., without being physically connected to a power source); a textile based electrochemical sensor configured to receive power from the rectified DC supply voltage and output an electric signal in response to one or more wound health data values of the associated wound fluid; a textile based VCO configured to receive power from the rectified DC supply voltage and modulate the electric signal output by the textile based electrochemical sensor into an RF frequency signal; and a second textile antenna configured to transmit the RF frequency signal modulated by the textile based VCO. The method can further comprise: applying the electronic system to a wound site in a patient, the wound site having an associated wound fluid; alternatively, applying the electronic system as part of a bandage, a dressing, or a covering conforming to a surface of the patient at or adjacent to the wound site; optionally, instructing the patient to wear the electronic system as long as the bandage, the dressing, or the covering is worn; powering the electronic system with the RF power signal; receiving the RF frequency signal from the electronic system; and determining a measured wound health data value based on the RF frequency signal. The method can further comprise: providing an interrogator; generating the RF power signal through the interrogator without contacting the electronic system; receiving the RF frequency signal into the interrogator without contacting the electronic system; obtaining from the interrogator an output corresponding to the measured wound health data value based on the RF frequency signal, the output being an auditory response, a visual response, or a haptic response; and/or making a wound healing assessment based on the interrogator output, the wound healing assessment being made by a healthcare professional in a formal healthcare environment; alternatively, the wound healing assessment being made by a healthcare professional, caregiver, or patient in a remote setting away from a formal healthcare environment. The measured wound health data value can be selected from pH of the wound, temperature of the wound, oxygenation of the wound, moisture of the wound, enzyme concentration of the wound, and uric acid concentration of the wound fluid.

In an embodiment, an electronic system for remote sensing and monitoring of wound healing in a wound having an associated wound fluid can comprise: a first textile antenna configured to receive an RF power signal; a fabric integrated rectifying circuit configured to convert the RF power signal to a rectified DC supply voltage, the electronic system being configured to operate normally without a power source (i.e., without being physically connected to a power source); a textile based electrochemical sensor configured to receive power from the rectified DC supply voltage and output an electric signal in response to one or more wound health data values of the associated wound fluid; a textile based VCO configured to receive power from the rectified DC supply voltage and modulate the electric signal output by the textile based electrochemical sensor into an RF frequency signal; and a second textile antenna configured to transmit the RF frequency signal modulated by the textile based VCO. The textile based electrochemical sensor can be an enzymatic biosensor configured to monitor levels of UA in the associated wound fluid. The enzymatic biosensor can comprise a WE, a CE, and a RE. The WE and the RE can be used to power the enzymatic biosensor with a sensor potential from the fabric integrated rectifying circuit; the WE and the CE can be connected to a sensor output resistor; the textile based VCO can be configured to read the DC voltage across the sensor output resistor; and the electronic system can optionally further include an interrogator and a back-end system, the interrogator configured to supply the RF power signal, receive the RF frequency signal, and relay the RF frequency signal to the back-end system for processing and data analysis. The textile based VCO can be configured to receive an input voltage in a range of from 0 V to 6 V and to provide an output frequency modulation at an output frequency of from 830 MHz to 1700 MHz, and the textile based electrochemical sensor and the textile based VCO can each be configured to receive power only from the RF power signal through the fabric integrated rectifying circuit. Alternatively, the RF frequency signal can be received directly by the back end processing system or another intermediate or terminal system, for example an intelligent or personal virtual assistant, digital assistant, smart phone, tablet, smart watch, or information appliance. Alternatively, the RF frequency signal may be relayed to another intermediate or terminal system, for example an intelligent or personal virtual assistant, digital assistant, smart phone, tablet, smart watch, or information appliance.

In an embodiment, a wound monitoring system to remotely sense and monitor electrochemical biomarkers from a wound bed having an associated wound fluid is disclosed can comprise: a textronic bandage; an interrogator; and a back-end system, the textronic bandage interfacing with the interrogator, and the interrogator interfacing with the back-end system. The textronic bandage can comprise: a first textile antenna configured to receive an RF power signal; a fabric integrated rectifying circuit configured to convert the RF power signal to a rectified DC supply voltage of less than 1.0 V, the textronic bandage being configured to operate normally without a power source (i.e., without being physically connected to a power source); a textile based electrochemical sensor further including: an enzymatic biosensor configured to receive power only from the rectified DC supply voltage and output an electric signal in response to levels of uric acid (UA) in the associated wound fluid, comprising a WE, a CE, and a RE, the WE and RE being used to power the enzymatic biosensor with a sensor potential of about –0.6 V only from the fabric integrated rectifying circuit, the WE and CE being connected to a sensor output resistor having a resistance value of about 350 k$\Omega$ and the VCO being configured to read the DC voltage across the sensor output resistor; a textile based VCO configured to receive power only from the rectified DC supply voltage and configured to modulate the electric signal given by the electrochemical sensor into an RF frequency signal at an output frequency of from 830 MHz to 1700 MHz; and a second textile antenna configured to transmit the RF frequency signal modulated by the VCO. The interrogator can comprise: a generator configured to create the RF power signal; an interrogator transmit antenna configured to deliver the RF power signal; an interrogator receive antenna configured to receive the RF frequency signal; a converter configured to convert the RF frequency signal into a transmissible signal including at least one data value; an interrogator communicator configured to relay the transmissible signal to the back-end; and an interrogator power supply configured to power at least the generator, converter, and communicator. The back-end system can comprise: a back-end communicator configured to receive the transmissible signal from the interrogator; a data management module configured to receive and store the at least one data value included in the transmissible signal; and a data processing and analysis module configured to process and analyze data including data analytics, data integration, and trend analysis with at least one of machine learning techniques or deep learning techniques.

BRIEF DESCRIPTION OF DRAWINGS

FIG. 4a is a schematic illustration of the voltage-controlled oscillator responsible for modulating the wound-data given by the electrochemical sensor, according to an embodiment of the subject invention.

FIG. 4b is a graphical illustration of the voltage-controlled oscillator responsible for modulating the wound-data given by the electrochemical sensor, according to an embodiment of the subject invention.

FIG. 5 is a chart showing data from testing of the VCO, according to an embodiment of the subject invention.

DETAILED DESCRIPTION

Figure 1:
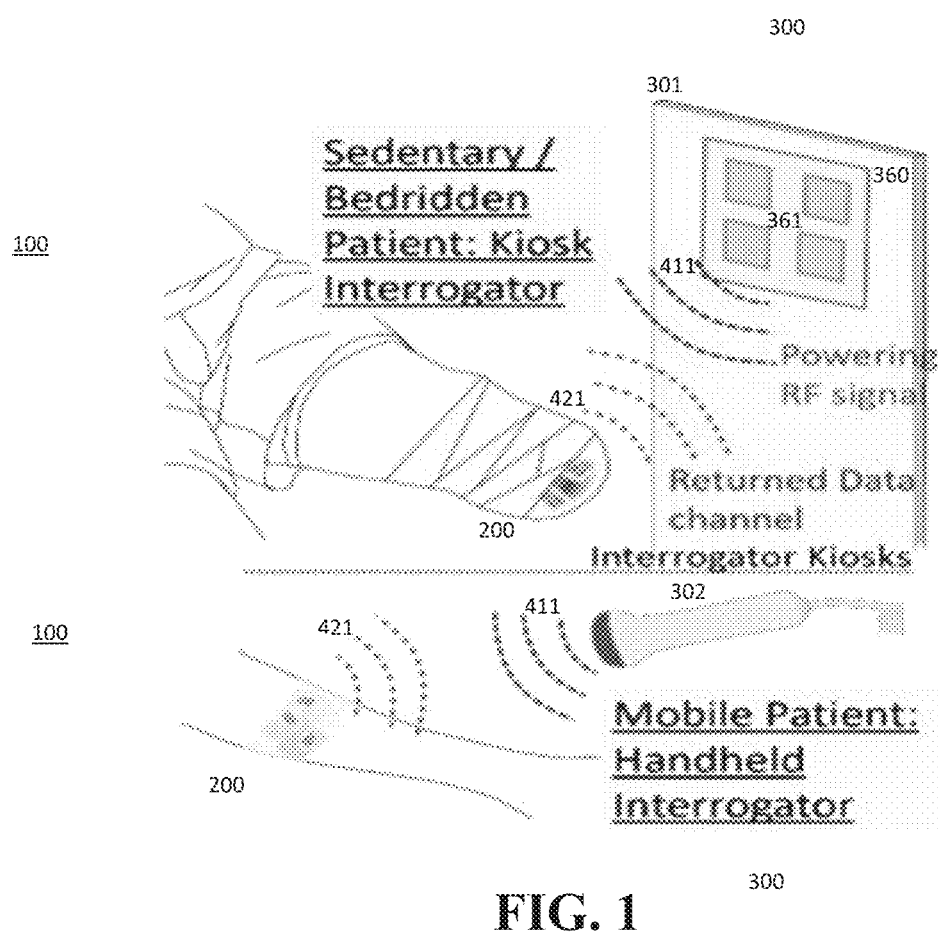
FIG. 1 is a graphical representation of a smart bandage and related systems and applications, according to an embodiment of the subject invention.

Embodiments of the subject invention provide novel and advantageous systems and methods to remotely sense and monitor electrochemical biomarkers including electrochemical solutions such as uric acid, cortisol (e.g., from sweat), enzyme, moisture, oxygen, as well as pH and temperature from a wound bed. In certain embodiments these biomarkers may be extracted from wound fluid and sweat and based on their levels, they may be used to help determine the wound status in terms of one or more parameters including, e.g., healing, infection occurrence, inflammation, and oxygenation.

Among therapeutic methods for chronic wounds, smart bandages can include circuits that can give an assessment on the healing status as well as treatment. To do so, smart bandages can feature electrochemical sensors that detect the level of bio-indicator/biomarker and modulate the wound-data to output something that can be interpreted by a patient, nurse, or a physician. Excellent sensors can be sensitive, selective, stable, and mechanically robust to assure durability.

Certain embodiments of the subject invention offer advantages over existing systems and methods including offering a more simplistic way to monitor or sense electrochemical solutions for quick and reliable assessment. In some embodiments a quick assessment may be derived via a frequency response emanated from the electric feedback of an electrochemical sensing device (sensor). The sensor may interface with a low-power voltage controlled oscillator (VCO) either alone or in combination with other electronics and illuminated by a low-power conversion rectifier that captures RF signals from, for example, an interrogator. Upon capturing the RF signals from the interrogator, the rectifier converts them into DC to feed both VCO and sensor. The sensor will sense the level of chemical solutions from the wound site or sweat and output an electric signal that is used to tune the voltage of the VCO. The VCO exhibits a frequency response that is modulated and transmitted back to the interrogator for assessment. The VCO response (frequency modulation) is used to develop an equation that enables quick and reliable assessment by non-technical individuals including patients, nurses, medical technicians, physicians. This eliminates the need for bulky and power-hungry electronics and offers seamless integration of fabric-based, low-power electronics to simplify the complex task of electrochemical assessment.

In certain embodiments a smart bandage is powered by a scanner that sends microwaves to the bandage. The bandage has an electronic circuit to convert microwaves into DC power to operate an electrochemical sensor that senses the level of uric acid from the wound fluid. The circuit also converts the concentration of uric acid into wireless signal transmitted back from the bandage to a remote receiver. This signal can be captured by a phone or other hand-held or portable device programmed to relay the severity and healing condition of the wound.

Embodiments of the subject invention have been tested by methods such as full wave simulation via 3D electromagnetic (EM) simulation software such as Ansys HFSS (High Frequency Structure Simulator, from ANSYS, Inc., 2600 Ansys Drive, Canonsburg, Pa. 15317 USA) to evaluate and then optimize the performance.

In certain embodiments of the subject invention, a smart bandage is provided for remote assessment of the healing process of chronic wound via data modulation. The assessment of the wound is made possible using fabric-integrated data modulation through the "transmit-reflect" principle as described by Vital et al. ("Electronic Wound Monitoring Using Fabric-Integrated Data Modulation," Antennas and Propagation & USNC/URSI National Radio Science Meeting, 2020 IEEE International Symposium), which is hereby incorporated by reference herein in its entirety. In certain embodiments an interrogator transmits a radio frequency (RF) signal to the smart bandage, which in turn, responds to the interrogator via its textile-based voltage-controlled oscillator (VCO). The VCO receives the DC electric signal from an electrochemical sensor that detects the level of (e.g.,) uric acid found in the wound bed. Based on the level of uric acid detected, the sensor outputs a changing DC signal that is fed to the VCO and is converted into a frequency-modulated signal. Each frequency detected from the output of the VCO corresponds to a specific uric acid concentration that was used for the assessment. For an accurate assessment a concentration threshold, such as 0.4 mM, reported in previous works, may be used to gauge the severity or the restoration of the damaged tissues. In certain embodiments the components of the bandage may relate to textile-based RF wireless power transfer and harvesting, electrochemical sensing, voltage-controlled oscillation or data modulation, and a protocol for quick and reliable assessment of chronic wounds, as well as the assembly of the smart bandage.

FIG. 1 shows a graphical representation of embodiments of the subject invention including a smart bandage and the related systems and applications. A wound monitoring system 100 to remotely sense and monitor electrochemical biomarkers from a wound bed via a textronic or smart bandage 200 interfacing with an interrogator 300 is shown. In the case of a bedridden or sedentary patient certain embodiments provide one or more interrogator kiosks 301 which provide a powering RF signal 411 from the interrogator to the bandage unit and may receive back information such as wound data over a returned data channel 421. The interrogator kiosks 301 may include a body 360 including one or more user interface elements 361, e.g., displays, keypads, buttons, speakers, or microphones. In the case of a mobile patient certain embodiments provide one or more handheld interrogators 302 which provide a powering RF signal 411 from the interrogator to the bandage unit and may receive back information such as wound data over a returned data channel 421. The handheld interrogators 302 may include a body 360 including one or more user interface elements 361, e.g., displays, keypads, buttons, speakers, or microphones.

Figure 2:
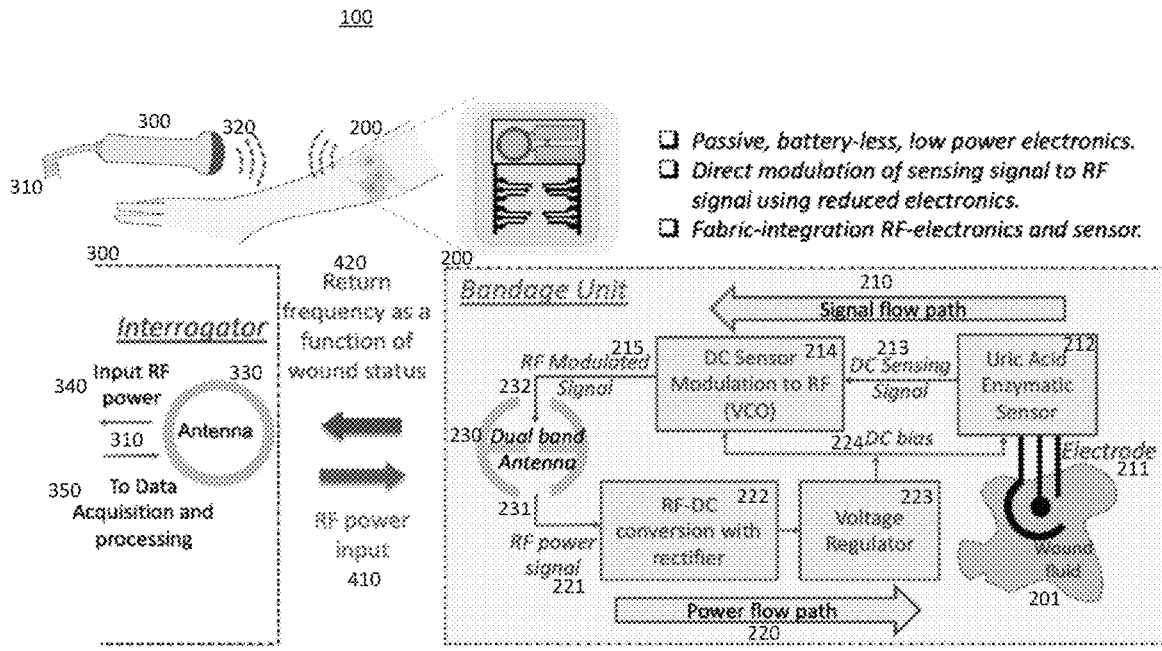
FIG. 2 is a graphical representation of a working principle of a smart bandage, according to an embodiment of the subject invention.

FIG. 2 shows a graphical representation of one embodiment of the subject invention including a working example of the proposed smart bandage remote monitoring system 100. Referring to FIG. 2, a smart textile bandage unit 200 is in communication with an interrogator 300 via a communication pathway 400. The interrogator 300 may have a corded or cordless connection 310 between an antenna 330 and either or both of a radio frequency (RF) power generator 340 and a data acquisition and processing unit 350.

The interrogator antenna 330 may communicate with the bandage unit antenna 230 via the communication pathway 400. Communications may include RF power input 410 from the interrogator to the bandage unit and wound data 420 including the return of frequency as a function of wound status from the bandage unit to the interrogator.

The bandage unit 200 may include a signal flow path 210 beginning with an electrode 211 in contact with the wound fluid 201 and at least one sensor 212, such as a uric acid enzymatic sensor. The sensor 212 may send a DC sensing signal 213 to voltage-controlled oscillator (VCO) 214 that takes the DC electric signal provided by electrochemical sensing of, e.g., the uric acid found in the wound fluid, and creates an RF modulated signal output 215.

The bandage unit antenna 230, e.g., a dual band antenna, has at least one input path 232 to receive the signal from the VCO. The bandage unit antenna also has at least one output path 231 to send, e.g., an RF power signal 221 received, e.g., as an RF power input 410, on to a power flow path 220 including an RF-DC conversion with rectifier 222. The rectifier 222 may supply a voltage regulator 223 which outputs a DC bias 224 to power the VCO 214 and sensor 212.

Figure 3:
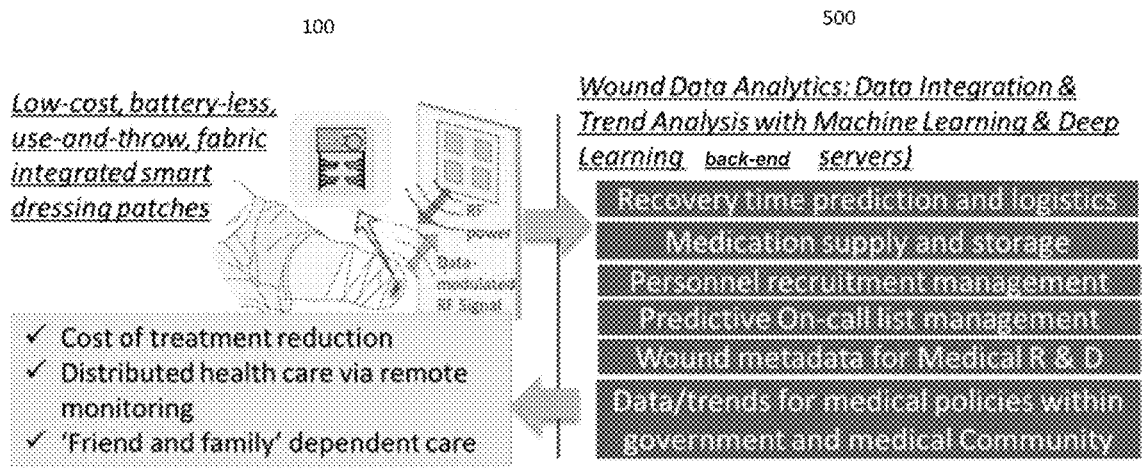
FIG. 3 is a graphical representation of a smart bandage and some advantages thereof, according to an embodiment of the subject invention.

FIG. 3 shows a graphical representation of one embodiment of the subject invention including a description of some advantages of the proposed smart bandage. The bandage unit 200 may include low-cost, battery-less, use-and-throw-away, fabric integrated smart dressing patches resulting in cost of treatment reduction, distributed healthcare via remote monitoring, or 'friend and family' dependent care. A wound monitoring system 100 may interface with a back-end system 500 to perform wound data analytics including data integration and trend analysis with machine learning and deep learning on, e.g., back-end servers. The back-end system 500 may also provide and/or support recovery time prediction and logistics, medication supply and storage, personnel recruitment and management, predictive on-call list management, wound metadata for medical R&D, and data/trends for medical policies within government and medical communities.

FIGS. 4a and 4b show a schematic illustration and a graphical illustration, respectively, of a finished voltage-controlled oscillator circuit 214 responsible for modulating the wound-data given by the electrochemical sensor as provided in one embodiment of the subject invention. This circuit diagram of the VCO 214 includes a connector 214a for receiving voltage V-tuning 214b connected to a Crystek CVCO055BE (Digi-Key Part Number 744-1112-ND) 214d and shunt capacitor C2, 214c. Connector 214f carries input voltage V-CC 214g connected to another input of the Crystek CVCO055BE (Digi-Key Part Number 744-1112-ND) 214d and shunt capacitor C1, 214e. Connecter 214h carries the signal RF-out 2141 from the VCO 214d.

FIG. 5 contains a chart of spectra shown as a sign of successful testing of the VCO for one embodiment of the subject invention. Modulated Spectra, power (in decibel-milliwatts (dBm)) is plotted on a scale from −120 dBm to 0 dBm vs. frequency (GHz). Series plots are largely overlapping in a range between about −90 dBm to about −75 dBm across all frequencies with frequent excursions down to −100 dBm and occasional excursions down to −105 dBm or lower as well as occasional excursions up to about −70 dBm across numerous individual frequencies and four notable sharp peaks cresting near or slightly above 0 dBm at about 0.83-0.84 GHz (attributed to 0.1V), at about 0.86-0.88 GHz (attributed to 0.4V), at about 0.90-0.92 GHz (attributed to 0.7V), at about 0.94-0.97 GHz (attributed to 1V) where the voltage levels of 0.1V, 0.4V, 0.7V, and 1V, respectively, represent DC voltage in to the VCO.

Figure 6A:
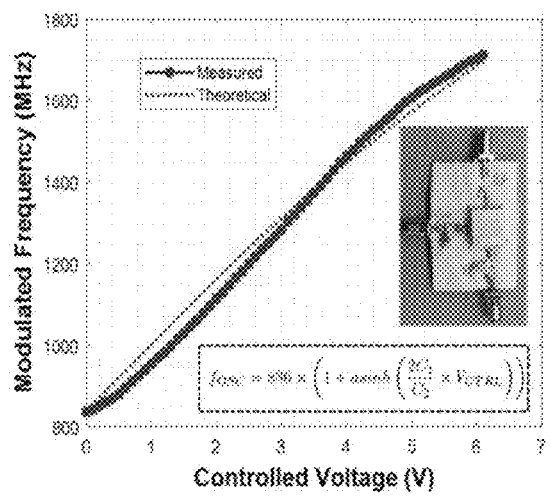
FIG. 6a is a chart showing frequency modulation resulted from the wound-data (by emulation) coming from the detection of the uric acid level, according to an embodiment of the subject invention.

FIG. 6a shows a chart showing frequency modulation resulted from the wound-data (by emulation) coming from the detection of the uric acid level in one embodiment of the subject invention. Modulated Frequency (MHz) is plotted in a range from 800 MHz to 1800 MHz vs Voltage (V) across a range from about 0 to about 6 Volts. Measured values are plotted against a theoretical curve created by the function:

$$f_{OSC} = 836 \times \left(1 + a\sinh\left(\left(\frac{2C1}{C2}\right) \times V_{CTRL}\right)\right)$$

Measured values track with the theoretical equation, starting equal at 0 volts; about 40 MHZ below the equation value of about 1000 MHz at about 1 volt; about 50 MHZ below the equation value of about 1160 MHz at about 2 volts; about 30 MHZ below the equation value of about 1310 MHz at about 3 volts; about equal with the equation value of about 1390 MHz at about 3.6 volts; about 20 MHZ above the equation value of about 1450 MHz at about 4 volts; about 40 MHZ above the equation value of about 1575 MHz at about 5 volts; and about 20 MHZ above the equation value of about 1700 MHz at about 6.1 volts. FIG. 6a also includes an inset depicting the VCO circuit used for the test.

Figure 6B:
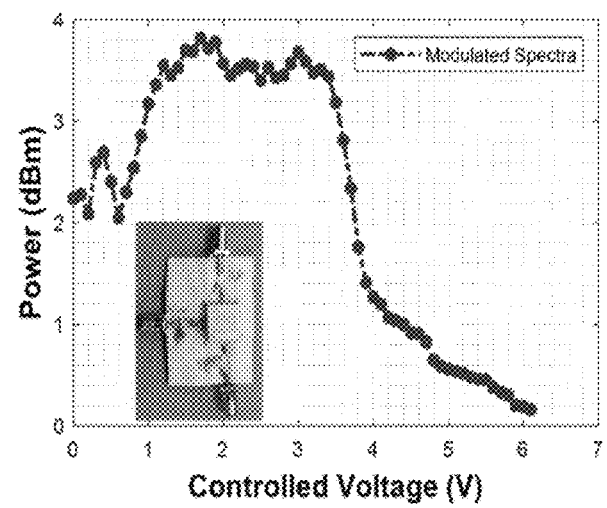
FIG. 6b is a chart showing power level of the spectra resulted from the modulation of the wound-data level, according to an embodiment of the subject invention.

FIG. 6b shows a chart showing power level of the spectra resulted from the modulation of the wound-data level in one embodiment of the subject invention. Modulated Spectra Power (dBm) is plotted in a range from about just less than 4 dBm to just above about 0 dBm vs Voltage (V) across a range from about 0 to about 6.1 Volts. Beginning at 2 and 3 dBm from 0 V up to about 1 V; the series peaks above about 3.4 dBm between 1 V and 3.4 V; drops sharply between 3.5 V and 4 V; then approximates and asymptotic approach towards 0 dBm between about 4 V and about 6 V. FIG. 6b also includes an inset depicting the VCO circuit used for the test.

Figure 6C:
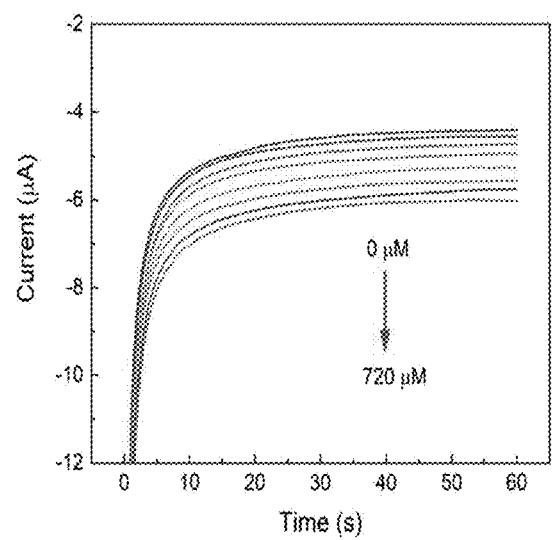
FIG. 6c is a chart showing sensor response to varying concentrations of uric acid, according to an embodiment of the subject invention.

FIG. 6c shows a chart showing sensor response current in μA versus time in seconds, to varying concentrations of uric acid in one embodiment of the subject invention. The current axis scale represents from −12 μA to −2 μA. The time scale represents 0-60 seconds. Five response curves are represented for concentrations from 0 μM to 720 μM, with each respective curve following a similar pattern, rising quickly between about 2 seconds and about 5 seconds before rounding to a mildly increasing but flatter trend between about 20 seconds and about 60 seconds. The fastest rising curve reached a response of about −6 μA in about 5 seconds before flattening out above −5 μA beyond about 20 seconds. The slowest rising curve reached a response of about −7 μA in about 10 seconds before flattening out above −6.5 μA beyond about 20 seconds.

Figure 6D:
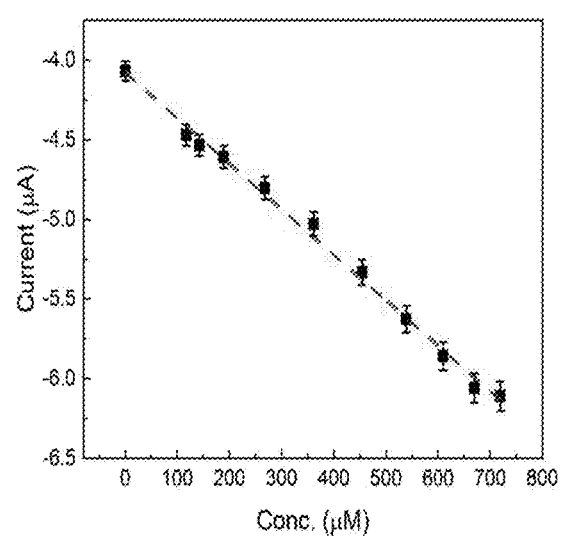
FIG. 6d is a chart showing a sensor calibration curve, according to an embodiment of the subject invention.

FIG. 6d shows a chart showing a sensor calibration curve used in one embodiment of the subject invention. Sensor current in μA is plotted on a scale from −6.5 μA to about −4 μA vs concentration ranging from about 0 μM to about 800 μM. A straight-line curve fit runs from about −4.1 μA at about 0 μM to about −6.1 μA at about 725 μM. Ten data points with error bars are shown along this linear curve.

Figure 7:
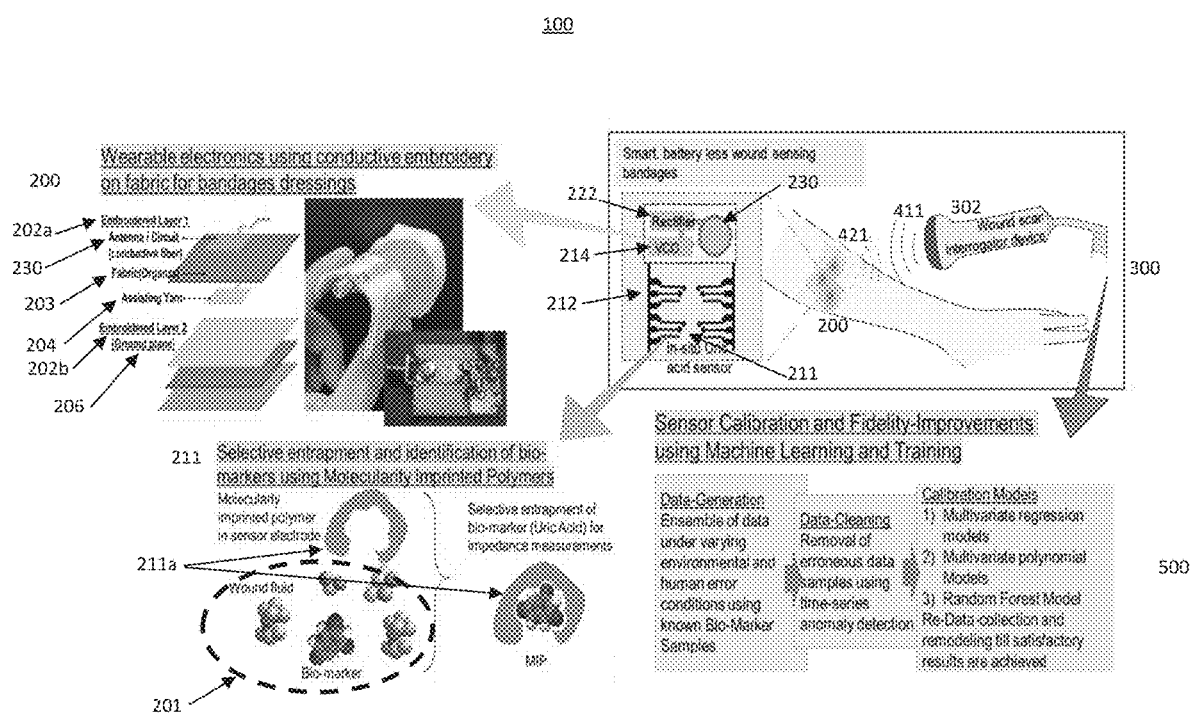
FIG. 7 is an exploded version of the power harvesting and sensing block of the smart bandage, according to an embodiment of the subject invention.

FIG. 7 shows an exploded version of the power harvesting and sensing block of the smart bandage in one embodiment of the subject invention, as well as expanded capabilities of the back-end system. Shown is a wound monitoring system 100 to remotely sense and monitor electrochemical biomarkers from a wound bed via a textronic or smart bandage 200 interfacing with a handheld interrogator 302 which provides a powering RF signal 411 from the interrogator to the bandage unit and may receive back information such as wound data over a returned data channel 421.

The smart bandage 200 may include wearable electronics using conductive embroidery on fabric for bandage dressings, such as those shown in FIG. 7, and may include a first embroidered layer 202a, antenna circuit 230 including conductive fiber, one or more fabric layers 203 (e.g., a thin, plain weave, sheer fabric made from silk or woven with synthetic filament fibers such as polyester or nylon, such as Organza), one or more features formed from an assisting yarn 204 (e.g., providing support or backing for features such as the antenna or connections within the circuit, or alternatively providing a layer of support and/or insulation between layers or between certain features of the wearable electronics circuit), one or more second embroidered layers 202b, and one or more ground plane layers 206. Insets to FIG. 7 show photographic or graphical representations of a wound sensing bandage The battery-less or remote powered smart bandage 200 may contain an antenna 230, a rectifier 222, a VCO 214, a sensor 212, and an electrode 211. The electrode 211 may be configured for selective entrapment and identification of biomarkers using molecularity imprinted polymers (MIPs) in the sensor electrode for selective entrapment of one or more biomarkers (e.g., uric acid) for impedance measurements. The system may also contain a back-end 500 including subsystems for sensor calibration, fidelity improvements, and other functions using machine learning and training. These may include data generation (e.g., collection of an ensemble of data under varying environmental and human error conditions using known bio-marker samples), data cleaning (e.g., removal of erroneous data samples using, e.g., time series anomaly detection), and calibration models including (1) multivariate regression models, (2) multivariate polynomial models, and (3) random forest model re-data-collection and remodelling till satisfactory results are achieved. FIG. 7 further illustrates how in some embodiments the data generation may feed into data cleaning, which then feeds into calibration models to produce an improved data model, algorithm, calibration, system, or system performance state.

Figure 8:
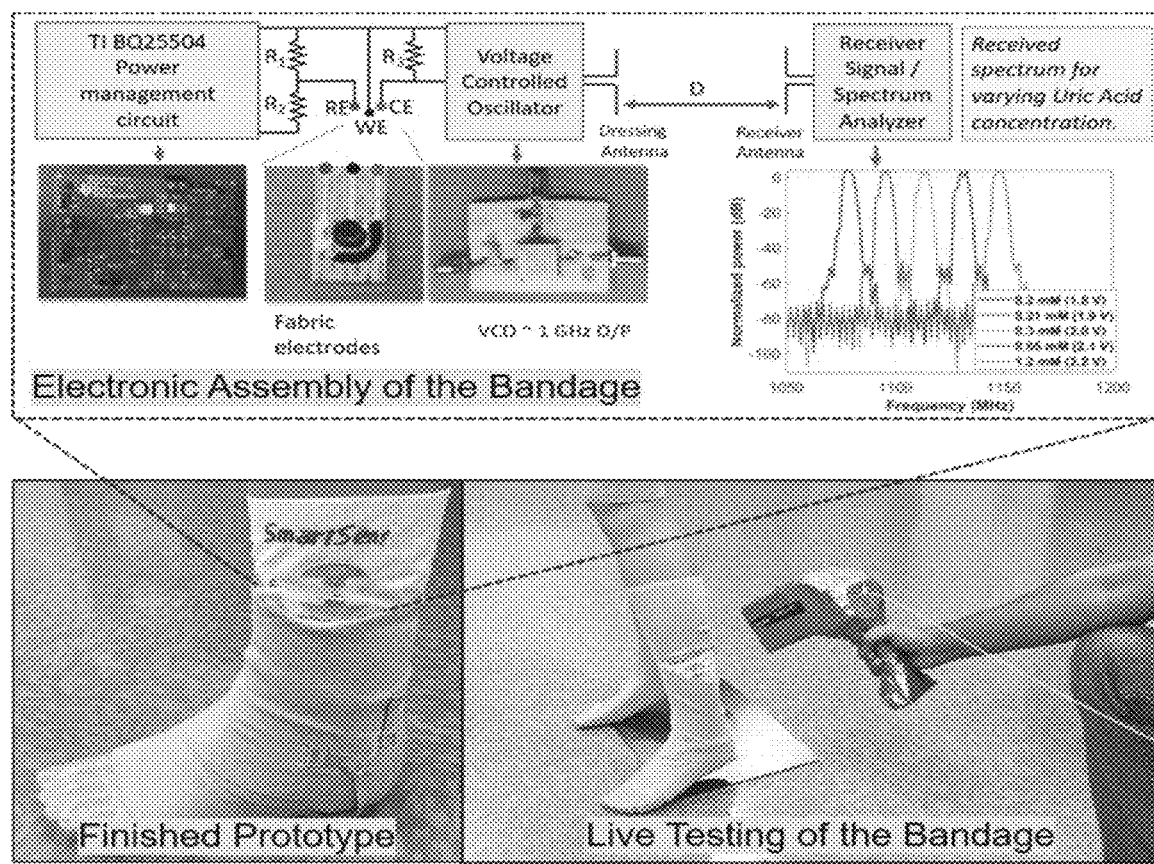
FIG. 8 is a representation of the internal electronic assembly of the smart bandage, according to an embodiment of the subject invention.

FIG. 8 shows a representation of the internal electronic assembly of the smart bandage in one embodiment of the subject invention as used to produce a finished system according to certain embodiments of the invention for live testing of the bandage. A power management circuit (PMC, e.g., TI BQ25504 Ultra-Low Power Boost Converter, Digi-Key Part Number 296-29741-2-ND) is connected to a VCO with resistors R1 and R2 providing desired voltage to fabric electrode RE, resistor R3 providing desired voltage to fabric electrode CE, and a direct connection to fabric electrode WE. The VCO circuit is powered by the PMC and feeds the dressing antenna. The dressing antenna communicates across an RF link to the receiver antenna which is connected to the receiver signal/spectrum analyser to receive the spectrum response for varying uric acid concentrations. Inset photographic or graphical images show actual prototype hardware used for the PMC, fabric electrodes, and VCO (~1 GHz O/P), respectively. A further inset shows receiver signal/spectrum analyser output as a chart of normalized power (dB) on a scale of −100 dB to 0 dB vs. frequency (MHz) on a scale from 1050 MHz to 1200 MHz. In this chart responses are generally around about −80 dB+/−about 10 dB across the range. Five distinct peaks in the response data are marked in a legend as (1) 0.2 mM (1.8 V) which rises up around about 1070 MHz, peaks around about 1075 MHz, and drops back down around 1090 MHz; (2) 0.21 mM (1.9 V) which rises up around about 1090 MHz, peaks around about 1095 MHz, and drops back down around 1110 MHz; (3) 0.3 mM (2.0 V) which rises up around about 1110 MHz, peaks around about 1115 MHz, and drops back down around 1125 MHz; (4) 0.65 mM (2.1 V) which rises up around about 1125 MHz, peaks around about 1130 MHz, and drops back down around 1140 MHz; (5) 1.2 mM (2.2 V) which rises up around about 1140 MHz, peaks around about 1145 MHz, and drops back down around 1155 MHz. All five peaks reach to the top of the scale, just above about 0 dB, or approximately about +0.2 dB and all five peaks both begin within and return back to an oscillating band ranging from about −70 dB to about −90 dB (with occasional excursions) across the range. Two additional photographs show (1) a finished system according to certain embodiments of the subject invention in place on the lower leg of a test mannequin and over-wrapped with a compressive bandage below, and (2) live testing of the bandage with the bandage again applied to the lower leg of a mannequin and over-wrapped above and below by a compressive bandage while being read with a handheld interrogator several inches away from the bandage while the mannequin maintains an active standing pose representing a patient whose smart bandage is read remotely, freely positioned, in a natural state, and without requiring a direct connection, contact, constrained motion, or rigid positioning.

Figures 9A, 9B, 9C, 9D:
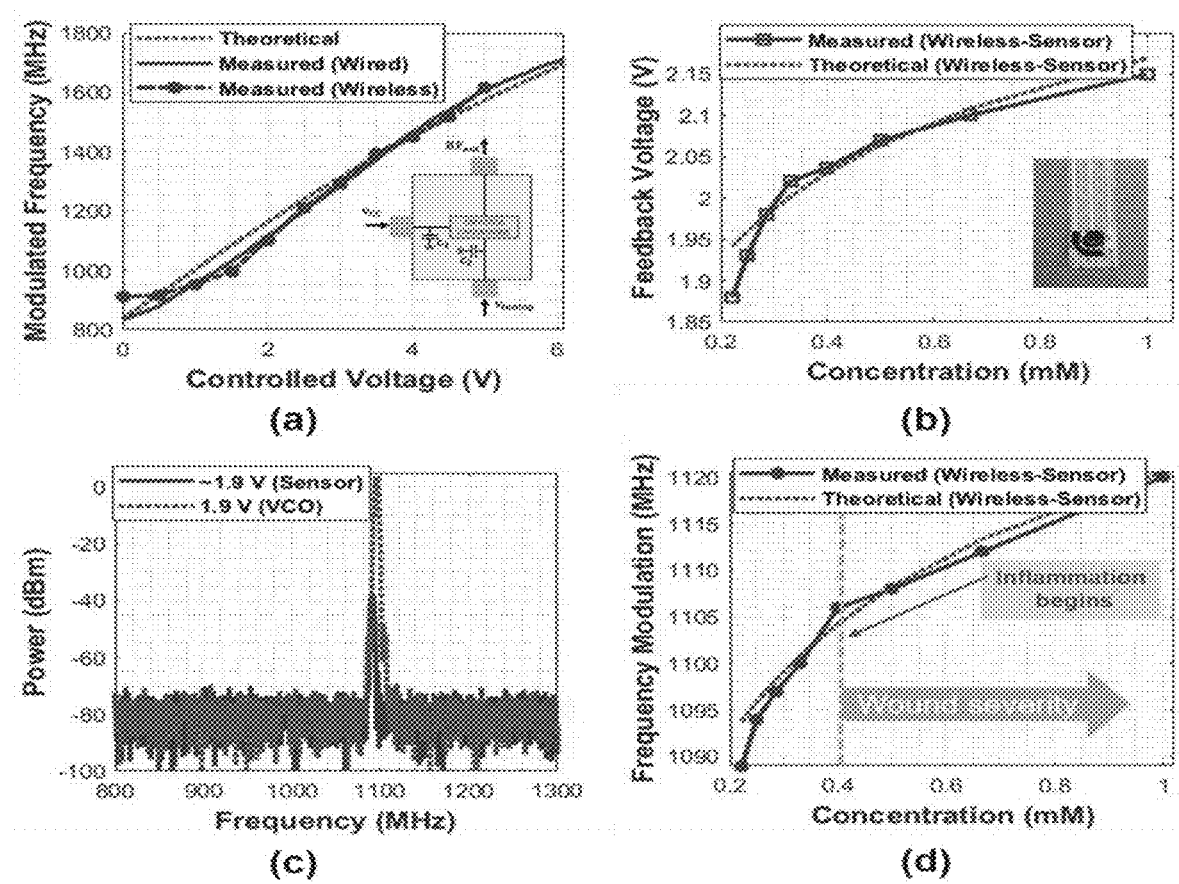
FIG. 9a is a chart showing a measurement from the textile-based VCO used in the modulation of the wound-data, used for the assessment of the wound status, according to an embodiment of the subject invention.
FIG. 9b is a chart showing wound data, given in the form of a DC signal by the electrochemical sensor, which will be used by the VCO for modulation, used for the assessment of the wound status, according to an embodiment of the subject invention.
FIG. 9c is a chart showing spectra for both wired and wireless testings of the bandage, used for the assessment of the wound status, according to an embodiment of the subject invention.
FIG. 9d is a chart showing the modulation of the wound-data realized for each uric acid level detected by the electrochemical sensor, used for the assessment of the wound status, according to an embodiment of the subject invention.

FIG. 9a shows a chart showing a measurement from the textile-based VCO used in the modulation of the wound-data, used for the assessment of the wound status in one embodiment of the subject invention. Modulated frequency response (MHz) is shown on a scale from about 800 MHz to about 1800 MHz vs a controlled voltage (V) on a scale from 0 V to about 6 V. The chart legend shows three data series. A theoretical curve of the predicted circuit response shows in a plain dashed line with a slight upward convexity between about 850 MHz at 0 V and about 1700 MHz at about 6 V. Next, a solid line without markings plots the measured (wired) response which originates in agreement with the dashed line at about 850 MHz at 0 V, continues slightly below the dashed line with a slight upward concavity until crossing slowly across the dashed line in the area around about 1400 MHz at about 3.4 V, then continues on above the dashed line and with a slight upward convexity until re-joining the dashed line at their common endpoint of about 1700 MHz at about 6 V. Finally, a dashed line with solid circular markings plots the measured (wireless) response which begins above the other two lines at about 900 MHz at 0 V, converges to and then slightly overshoots the solid line of the measured (wired) curve between around 1 V and around 2 V, displaying a slightly greater upward concavity before closely following the solid line as it crosses over the dashed line before settling back to a common endpoint of all three curves at about 1700 MHz at about 6 V. An inset on the chart shows a schematic diagram similar to the VCO circuit of FIG. 4a.

FIG. 9b shows a chart showing wound data, given in the form of a DC signal by the electrochemical sensor, which will be used by the VCO for modulation, used for the assessment of the wound status in at least one embodiment of the subject invention. Feedback voltage (V) is shown on a scale from 1.85 V to 2.15 V versus a concentration (mM) from 0.2 mM to about 1 mM. Two series are shown on the chart legend. A solid line with square markings represents measured (wireless sensor) values and a dashed line with no markings represents theoretical (wireless sensor) values. The dashed line of the theoretical curve begins just below 1.95 V at a point just above 0.2 mM concentration, rising upward but concave down across the range, and transitioning from a steeper positive slope below about 0.4 mM concentration to a flatter positive slope above about 0.6 mM concentration before ending at about 2.17 V at about 1 mM concentration. The solid line with square markings of the measured (wireless sensor) response begins below the dashed line of the theoretical curve at about 1.88 V just above about 0.2 mM concentration, rises rapidly to a point above the dashed line of about 2.02 V at about 0.33 mM concentration, then flattens and continues in a reduced but still positive slope until terminating at about 2.15 V at about 1 mM concentration. An inset on the chart shows a photograph of the fabric electrodes of FIG. 8.

FIG. 9c shows a chart showing spectral response in one embodiment of the subject invention. The chart shows Power (dBm) on a scale from −100 dBm to about 0 dBm vs frequency on a scale from 800 MHz to 1300 MHz. A legend on the chart shows two series, ~1.9 V (Sensor) represented by a solid line and 1.9V (VCO) represented by a dashed line. Both series oscillate rapidly around about −85 dBm+/−10 dBm with occasional excursions across the entire range. Both series also show a spike between about 1080 MHz and about 1100 MHz. The solid line of the sensor series values demonstrate a peak earlier, at around −40 dBm before returning to about −85 dBm+/−10 dBm while dashed line of the VCO series peaks at about 0 dBm before returning to baseline.

FIG. 9d shows a chart showing the modulation of the wound-data realized for each uric acid level detected by the electrochemical sensor, used for the assessment of the wound status in one embodiment of the subject invention. The chart shows frequency modulation (MHz) on a scale from about 1090 MHz to about 1120 MHz vs concentration (mM) on a scale from about 0.2 mM to about 1 mM. The chart legend shows two series, a solid line with solid circular markers representing measured (wireless-sensor) values and a dashed line without markings representing theoretical (wireless-sensor) values. The dashed line of the theoretical curve begins just below about 1095 MHz at a point just above 0.2 mM concentration, rising upward but concave down across the range, and transitioning mildly from a slightly steeper positive slope below about 0.4 mM concentration to a moderately flatter positive slope above about 0.6 mM concentration before ending at about 1120 MHz at about 1 mM concentration. The solid line with solid circular markings of the measured (wireless sensor) response begins below the dashed line of the theoretical curve at a value just below about 1090 MHz at just above about 0.2 mM concentration, rises rapidly to a point above the dashed line of about 1106 MHz at about 0.4 mM concentration, then flattens and continues in a reduced but still positive slope until terminating at about 1120 MHz at about 1 mM concentration. The solid line continues in a near-linear fashion, dropping below the dashed line after crossing at about 1108 MHz at around 0.5 mM concentration and remaining below the convex-up dashed line until co-terminating at about 1120 MHz at about 1 mM concentration. A vertical dashed line is present at about 0.4 mM concentration with a label indicating wound severity increasing with increasing concentration (of, e.g. uric acid) to the right and a second note marking inflammation begins at this same line at about 0.4 mM.

Figures 10A, 10B, 10C, 10D:
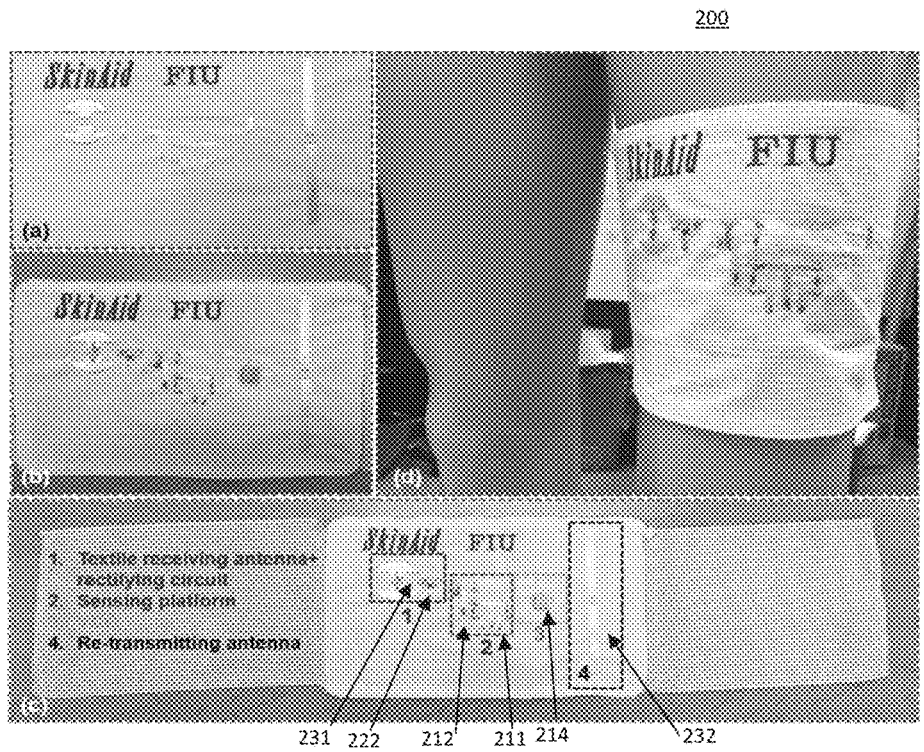
FIG. 10a is a graphical depiction of a developed system with associated circuits including a full-view of the system developed from the automated embroidery of conductive textiles onto fabric substrates, according to an embodiment of the subject invention.
FIG. 10b is a graphical depiction of a developed system with associated circuits including a finished system with full circuit realization, according to an embodiment of the subject invention.
FIG. 10c is a graphical depiction of a developed system with associated circuits including identification of different circuits constituting the bandage, according to an embodiment of the subject invention.
FIG. 10d is a graphical depiction of a developed system with associated circuits including a finished system of smart bandage placed on human leg showing the practicality of clinical application, according to an embodiment of the subject invention.

FIG. 10a shows a graphical depiction of a developed system with associated circuits including a full view of the system developed from the automated embroidery of conductive textiles onto fabric substrates in one embodiment of the subject invention.

FIG. 10b shows a graphical depiction of a developed system with associated circuits including a finished system with full circuit realization in one embodiment of the subject invention.

FIG. 10c shows a graphical depiction of a developed system with associated circuits including identification of different circuits constituting the bandage in one embodiment of the subject invention.

Referring to FIG. 10c, a smart bandage 200 according to certain embodiments of the subject invention is shown, including a complete and functional circuit built up from the embroidered elements of FIG. 10a, adding the electronic components additionally shown in FIG. 10b, and finally in simulated use in a clinical patient setting in FIG. 10d. The system includes (1) a textile receiving antenna and rectifying circuit including a receiving antenna with input path 231 for receiving RF energy from the interrogator, and rectifying circuit 222; (2) a sensing platform including a sensor 212 (e.g., a uric acid enzymatic sensor) and an electrode 211; (3) a VCO circuit including a VCO 214; and (4) a re-transmitting antenna section including an output path 232 for transmitting RF modulated signal information back to the interrogator.

FIG. 10d shows a graphical depiction of a developed system with associated circuits including a finished system of smart bandage placed on human leg showing the practicality of clinical application in one embodiment of the subject invention.

Figure 11:
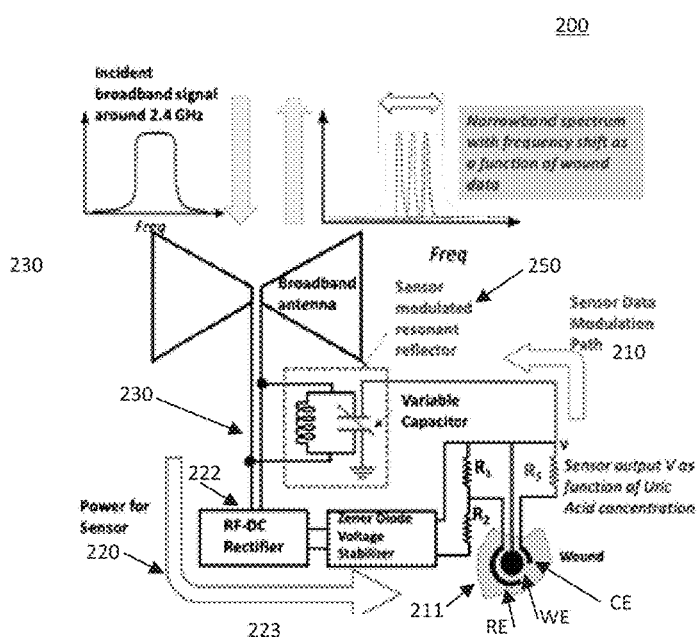
FIG. 11 is a schematic representation of a completely passive smart bandage using only a varactor for data modulation, according to an embodiment of the subject invention.

FIG. 11 shows a schematic representation of a completely passive smart bandage 200 using only a varactor for data modulation in one embodiment of the subject invention. The system begins operation with an incident broadband signal (e.g., around 2.4 GHz) excites the dual band broadband antenna 230, sending RF energy down the input path 231 to the DC rectifier 222, providing power for the sensor through the power flow path 220. A Zener diode voltage stabilizer acts as the voltage regulator 223 and resistors R1, R2, and R3 modulate the voltage between three fabric sensor electrodes, RE, WE, and CE, respectively which form all or part of the electrode 211 in contact with the wound fluid 201 and feeding a sensor output voltage V as a function of uric acid concentration in the wound fluid along the sensor data modulation path where a sensor modulated resonant reflector circuit 250 includes a variable capacitor in parallel with an inductor bringing the modulated output signal back to the dual band broadband antenna 230. A narrowband spectrum with frequency shift as a function of wound data is then transmitted back to the interrogator.

In this example, RFID-like functionality may be achieved using only passive circuitry while modulating DC sensor data into an RF signal which can be transmitted back to the interrogator with a reduced number of passive components and no active components; thus resulting in reduced cost, complexity, and power requirements for the smart bandage while providing compatibility with all electrochemical sensor types including cortisol, glucose, and uric acid via enzymatic or other types of sensor.

Figure 12:
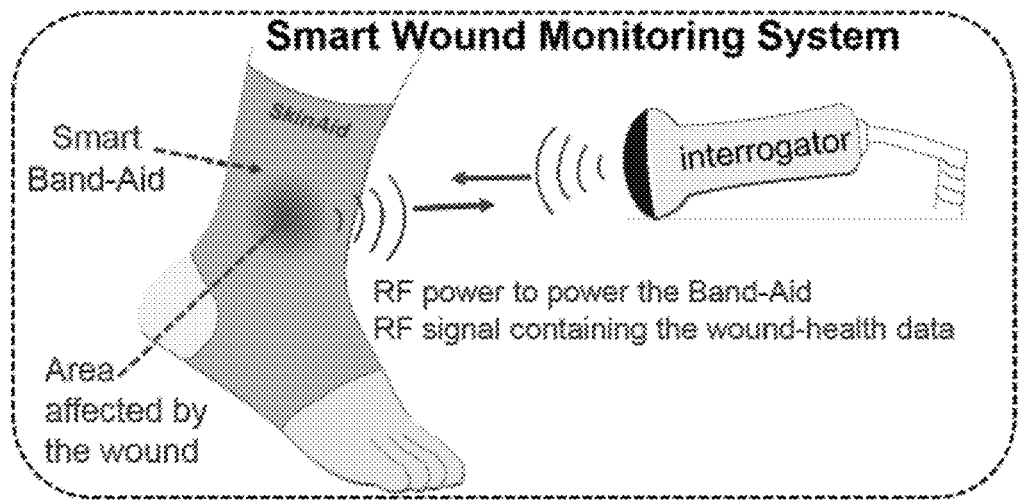
FIG. 12 is a graphical representation of a smart band aid or bandage that responds to interrogator power signal by reflection of the data-signal containing the wound-health data back to the interrogator, according to an embodiment of the subject invention.

FIG. 12 shows a graphical representation of a smart band aid or bandage that responds to interrogator power signal by reflection of the data-signal containing the wound-health data back to the interrogator in one embodiment of the subject invention. In this embodiment the smart bandage is placed directly on or adjacent the wound. An RF power signal from an interrogator powers the smart bandage remotely and drives in response an RF signal containing wound health data back from the smart bandage to the remoter interrogator. Data collection via the interrogator is quick and easy, requiring no portable power on the smart bandage itself as power is driven from the interrogator. Further, the wound data can be read without disturbing or removing the bandage. This low power, non-contact, and non-invasive collection of wound data allows for frequent, non-obtrusive, remote monitoring of the wound data to improve patient care.

Figure 13:
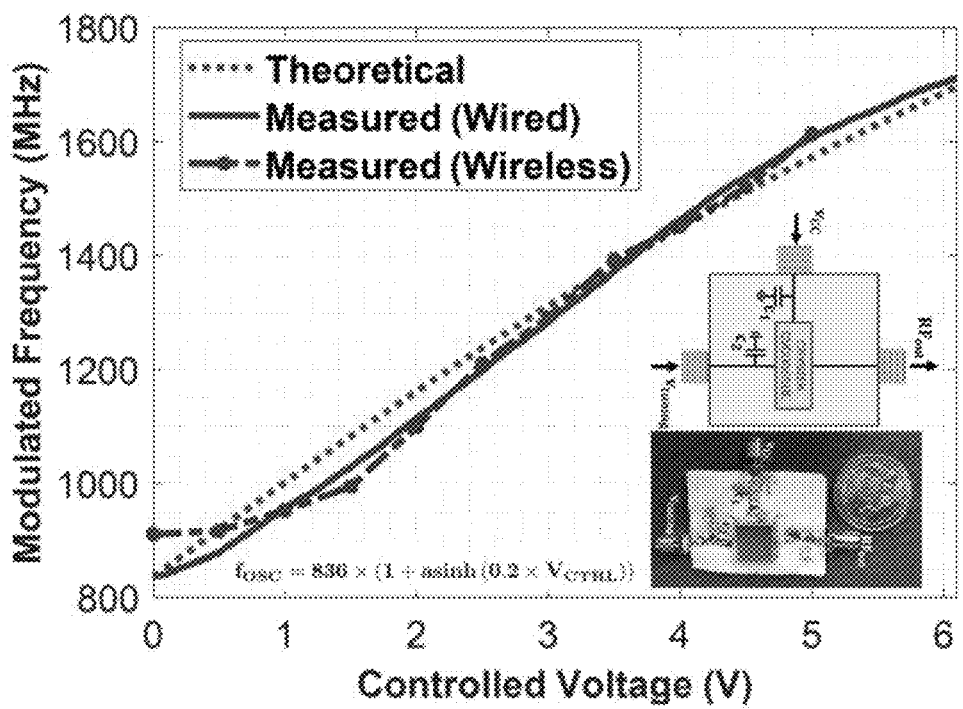
FIG. 13 is a chart with insets showing characterization of the textile-based VCO: (in inset: circuit diagram and finished system of the circuit) theoretical (with equation in inset), and measured frequency modulations provided by the VCO using the result of the electrochemical sensing of the wound fluid for both wired and wireless data transfer (where in this experiment, VCTRL=Vtuning), according to an embodiment of the subject invention.

FIG. 13 shows a chart with insets showing characterization of the textile-based VCO: (in inset: circuit diagram and finished system of the circuit) theoretical (with equation in inset), and measured frequency modulations provided by the VCO using the result of the electrochemical sensing of the wound fluid for both wired and wireless data transfer (where in this experiment, VCTRL=Vtuning) in one embodiment of the subject invention. The chart showing frequency modulation resulted from the wound-data coming from the detection of the uric acid level in one embodiment of the subject invention. Modulated Frequency (MHz) is plotted in a range from 800 MHz to 1800 MHz vs Voltage (V) across a range from about 0 to about 6 Volts. Measured values are plotted against a theoretical curve created by the function:

$$f_{osc}=836\times(1+a\sin h(0.2\times V_{CTRL}))$$

The chart legend of FIG. 13 shows three data series. A theoretical curve of the predicted circuit response shows in a plain dashed line with a slight upward convexity between about 850 MHz at 0 V and about 1700 MHz at about 6 V. Next, a solid line without markings plots the measured (wired) response which originates in agreement with the dashed line at about 850 MHz at 0 V, continues slightly below the dashed line with a slight upward concavity until crossing slowly across the dashed line in the area around about 1400 MHz at about 3.4 V, then continues on above the dashed line and with a slight upward convexity until rejoining the dashed line at their common endpoint of about 1700 MHz at about 6 V. Finally, a dashed line with solid circular markings plots the measured (wireless) response which begins above the other two lines at about 900 MHz at 0 V, converges to and then slightly overshoots the solid line of the measured (wired) curve between around 1 V and around 2 V, displaying a slightly greater upward concavity before closely following the solid line as it crosses over the dashed line before settling back to a common endpoint of all three curves at about 1700 MHz at about 6 V. A pair of insets on the chart shows a schematic diagram similar to the VCO circuit of FIG. 4a and a photograph showing a circuit similar to that shown in FIG. 4b.

Figure 14:
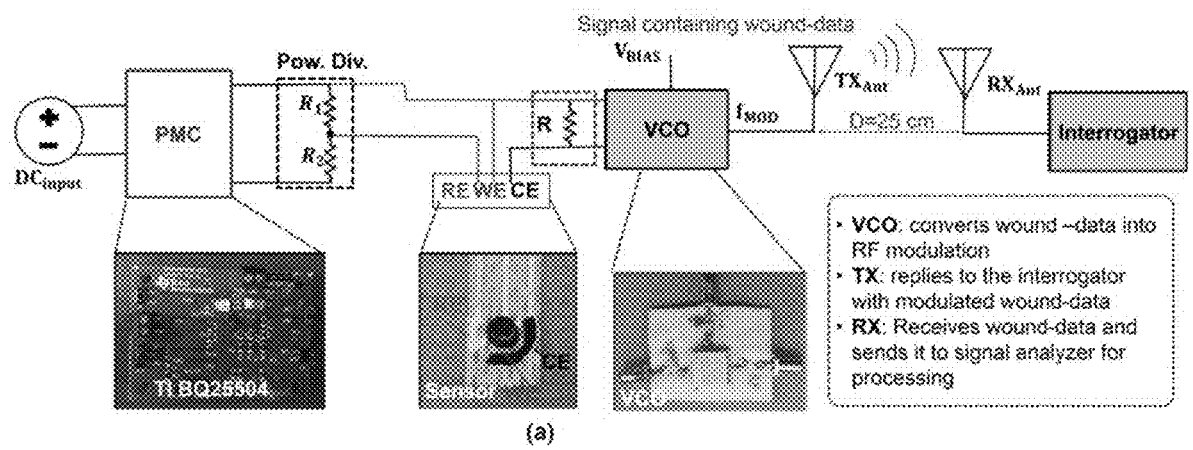
FIG. 14 is a schematic representation of the proposed smart textronic developed with the integration of on-fabric circuits emulating the wound healing assessment including a complete diagram of the system with all associated components, according to an embodiment of the subject invention.

FIG. 14 shows a schematic representation of the proposed smart textronic developed with the integration of on-fabric circuits emulating the wound healing assessment including a complete diagram of the system with all associated components in one embodiment of the subject invention. In this figure the electronic assembly of the bandage (substantially as shown and described in FIG. 8) feeds a frequency modulated signal containing wound-data to the TX-antenna at a nominal distance (e.g., 25 cm) from the RX-antenna on the interrogator. The VCO converts wound-data into RF modulation. The TX replies to the interrogator with modulated wound data. The RX receives wound-data and sends it to a signal analyzer for processing.

Figure 15:
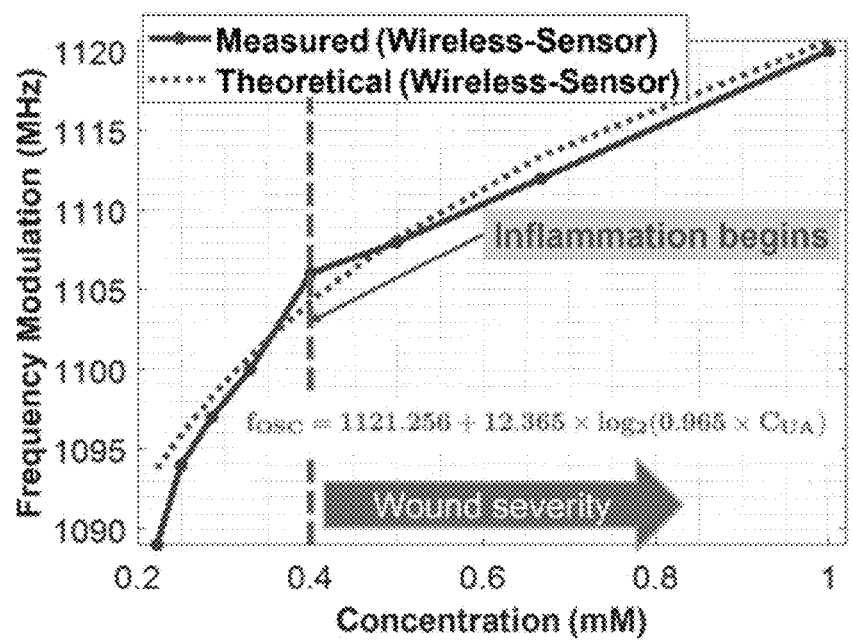
FIG. 15 is a chart depicting a wound-healing assessment using feedback response of the sensor in terms of frequency modulation (theoretical—with equation displayed in inset and measured results) to interpret the detection of the wound fluid concentration, according to an embodiment of the subject invention.

FIG. 15 shows a chart depicting a wound-healing assessment using feedback response of the sensor in terms of frequency modulation (theoretical—with equation displayed in inset and measured results) to interpret the detection of the wound fluid concentration in one embodiment of the subject invention. The chart shows frequency modulation (MHz) on a scale from about 1090 MHz to about 1120 MHz vs concentration (mM) on a scale from about 0.2 mM to about 1 mM. The chart legend shows two series, a solid line with solid circular markers representing measured (wireless-sensor) values and a dashed line without markings representing theoretical (wireless-sensor) values. The dashed line of the theoretical curve begins at about 1094 MHz at a point just above 0.2 mM concentration, rising upward but concave down across the range, and transitioning mildly from a slightly steeper positive slope below about 0.4 mM concentration to a moderately flatter positive slope above about 0.6 mM concentration before ending at about 1120 MHz at about 1 mM concentration. The solid line with solid circular markings of the measured (wireless sensor) response begins below the dashed line of the theoretical curve at a value just below about 1090 MHz at just above about 0.2 mM concentration, rises rapidly to a point above the dashed line of about 1106 MHz at about 0.4 mM concentration, then flattens and continues in a reduced but still positive slope until terminating at about 1120 MHz at about 1 mM concentration. The solid line continues in a near-linear fashion, dropping below the dashed line after crossing a second time at about 1108 MHz at around 0.5 mM concentration and remaining below the convex-up dashed line until co-terminating at about 1120 MHz at about 1 mM concentration. A separate, bolder, vertical dashed line is present at about 0.4 mM concentration with a label indicating wound severity increasing with increasing concentration (of, e.g. uric acid) to the right and a second note marking inflammation begins at this same line at about 0.4 mM. The theoretical curve equation is given on an inset to the chart, as:

$$f_{osc} = 1121.256 + 12.365 \times \log_2(0.965 \times C_{UA})$$

In certain embodiments the biomarkers used may include pH of the wound, its temperature, its oxygenation, its moisture, its enzyme, and its level of uric acid as discussed in Pal et. al., Biosensors and Bioelectronics, 2018, 117, 696-705; Derakhshandeh et. al., Trends in biotechnology, 2018, 36(12), 1259-1274; and Kassal et. al., Electrochemistry Communications, 2015, 56, 6-10; each of which is hereby incorporated by reference herein in its respective entirety. Without limiting the scope of the subject invention, one biomarker that is proven to be reliable and thus may be used in certain embodiments is uric acid where a threshold of 0.4 mM may be used to gauge the severity or the restoration of the damaged tissue as discussed in Fernandez et. al., Current rheumatology reports, 2014, 16(2), 396; and Fernandez et. al., International wound journal, 2012, 9(2), 139-149; each of which is hereby incorporated by reference herein in its respective entirety. Several smart bandages have been developed using uric acid as a biomarker such as in Derakhshandeh et. al., Trends in biotechnology, 2018, 36(12), 1259-1274; and Kassal et. al., Electrochemistry Communications, 2015, 56, 6-10; each of which is hereby incorporated by reference herein in its respective entirety. Many such smart bandages use complex circuits including a potentiostat as described in Kassal, or a RF transceiver and microcontroller (e.g., Arduino) in order to detect the level of uric acid and wirelessly transmit it to a remote receiver. These circuits are power hungry, and a conventional Li-ion battery is often used to power them. Certain embodiments of the subject invention reduce the hardware of the system by replacing the Li-ion battery by a wireless power transfer and harvesting to operate the sensor whose wound-data signal may be sent to any remote receiver using a voltage-controlled oscillator and an antenna. In these embodiments, some or all of the circuits are built on textile in order to achieve conformability with human body instead of having PCB as described, e.g., in Pal (2018) and Kassal (2015).

Certain embodiments, including those illustrated in FIG. 1, include the "transmit-reflect" principle where an interrogator may be use to transmit RF power to the smart bandage at a given frequency. This power, arriving at the smart bandage may then be converted into DC power via the RF-to-DC conversion capacity of the rectifying circuit. The output power that is available at the resistive load of the rectifying circuit may then be branched out to power the electrochemical sensor and the voltage-controlled oscillator (VCO) found also on the bandage. The electrochemical sensor (ES) may be dipped in, contacted with, or exposed to the wound fluid to detect the level of, e.g., uric acid (UA) present in the wound and output it as a DC signal to be captured by the VCO. The VCO, upon modulation of these DC signals, may send them to a response-antenna to transmit them back to the interrogator where the assessment of the wound will be realized as every RF signal that is arrived at the interrogator may be correlated to a unique level of uric acid detected by the electrochemical sensor.

In certain embodiments the smart bandage may be representative of a smart dressing system as shown in FIG. 2 that combines fabric-integrated wireless power transfer and harvesting, electrochemical sensing, data-modulation, and transmit-reflect module. The wireless power transfer may feature misalignment-resilient antennas know as anchor-shaped to transmit and receive power from the interrogator and assure good transmission/reception of power in common clinical settings and/or scenarios as the bearer of the bandage will be free to move while getting power from the interrogator. The harvesting system may be responsible to realize the conversion of RF power into DC that is usable to operate both electrochemical sensor and VCO. This special power transfer and harvesting system may in some embodiments require only one diode to rectify close to 80% of power as well as utilizing a low-profile antenna to provide high power transfer efficiency even under misaligned conditions as described by Vital et al., 2020, IEEE/MTT-S International Microwave Symposium (IMS) (pp. 1184-1187); Vital et al., IEEE Transactions on Antennas and Propagation, doi: 10.1109/TAP.2020.3030976; and Vital et al., in IEEE Transactions on Microwave Theory and Techniques, doi: 10.1109/TMTT.2020.3029530; each of which is hereby incorporated by reference herein in its respective entirety. The electrochemical sensor may include those described by Umasankar, 2018, October, IEEE SENSORS (pp. 1-4). IEEE, which is hereby incorporated by reference herein in its entirety. In certain embodiments the sensor may also be prototyped on fabric and selected, configured, or tuned to achieve a sensitivity which will only allow the detection of a selected biomarker from the variety of them present in the wound bed. The data modulation may be done through a simplistic system that only features a textile based VCO to transform DC signals into RF signals in order to avoid complex circuits in the bandage. In some embodiments the transmit-reflect module can comprise a single antenna (e.g., an omnidirectional antenna) that will send the modulated signals to any remote receiver (e.g., the interrogator) for assessment. In some embodiments the assessment may be communicated to a healthcare professional, a caregiver, a layperson, or the patients themselves based on a simple screen-reading. It is contemplated within the scope of embodiments of the subject invention that:

a) The system will power the circuit featured in the bandage wirelessly.

b) The system uses an all-textile electrochemical sensor that is conformal to patient body surfaces including legs, arms, forearms, back, feet, wrist, and the like.

c) The system uses textile-based VCO as a simple, reliable, power efficient, and cost effective circuit to realize the modulation of the wound-data for sending back to the interrogator or any remote receiver through transmit-reflect single antennas.

d) The system comprises low-power circuits that are suitable for applications in body-worn circuits/devices.

Certain embodiments of the subject invention yield multifaceted advantages as shown in FIG. 3, which can include low or reduced cost, lowered or reduced power and/or battery requirements, peel-n-stick reusable and single use configurations, fabric-integrated dressing solutions for wound care. By using this system or method, the user will be able to save treatment cost, eliminate transportation and in-person visitation while staying home and enjoy the care they deserve, and reduce the frequency of need for a healthcare professional to assess the healing status of their conditions. Certain embodiments of the present invention will further enable reliable wound-data analytics that can perform the prediction of recovery time and logistics and provide the ability to notify their caregivers of a present or developing emergency situation. Certain embodiments of the subject invention also provide a model that can enable a non-tech savvy individual to quickly and reliably understand the healing process of the wound.

Certain embodiments of the subject invention provide a smart fabric-integrated electronic used for effective chronic wound healing assessment based on the concentration threshold (0.4 mM) reported in Fernandez, et. al., 2012. The system operates in these embodiments by responding to an interrogator with the wound-data in the form of modulated signal. The system in these embodiments further uses an on-fabric VCO responsible for the RF modulation sensor DC signal, which can be transmitted through an antenna. This re-transmission of the electric signal may be accomplished through a patch antenna placed at 25 cm away from the receiver (another patch) connected to a signal analyzer to display the spectrum. For quick and effective monitoring, a model of the RF modulation of the wound-data is developed. This smart system beneficial due to its cost-efficiency, ease to fabricate and use, and the model developed for quick and reliable assessment.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1—Textile-Based VCO

In FIGS. 4a and 4b, one exemplary embodiment of a textile based VCO is presented. This system was made of conductive textiles (Elektrisola-7) embroidered onto denim fabric. The circuit uses a Crystek CVCO055BE chip to convert DC wound-data into modulated RF signals for re-transmission back to the interrogator or any remote receiver. Two capacitors $C_1=1$ nF and $C_2=10$ nF as well as the DC-bias voltage $V_{cc}=3.14$ V are used to calibrate the IC. The performance of the VCO was tested for tuning voltages ranging from 0 to 6.2 V. These voltages emulate the output of the electrochemical sensor based on the concentration of the uric acid that is detected from the wound fluid, as shown in FIG. 5. As can be seen in FIG. 5, each voltage level corresponds to an output RF signal to be sent to the remote receivers. The voltages in the range of 0 to 6.2 V yield a frequency ranging from 836 MHz to 1.712 GHz as shown in FIG. 6a). In this example, these spectra (from 0.15 dBm to 3.8 dBm) are displayed on a Keysight PXA signal analyzer N9030B to emulate the remote receiver. This VCO, realized via automated embroidery of textiles onto fabric substrates uses very few components and the circuit assembly is very compact to facilitate usage on a wide variety of bandage or wound dressing applications. In this embodiment the VCO enables conversion of the DC wound-data given by the electrochemical sensor into RF signals carrying information necessary for the assessment of the wound. The simple, compact, reliable, power efficient, and cost effective circuit of this embodiment of the subject invention replaces the plurality of circuits that are used by current bandages, helps reduce the complexity of the data-modulation circuit, and provides quick and reliable results. It does not require any type of post-processing that requires heavy and expensive equipment to perform. One empirical equation that is developed for this VCO is the following:

$$f_{oscillation} = 836 \times \left(1 + a\sinh\left(\frac{2C_1}{C_2} \times V_{tuning}\right)\right) \quad \text{Equation 1}$$

Example 2—Textile-Based Electrochemical Sensor

The sensor shown in FIG. 7 and used in this embodiment is a 3-electrode flexible enzymatic sensor fabricated using screen printing of conductive ink onto gauze fabric. This sensor was fabricated to be used on wound dressings using a multilayer screen-printing approach, wherein conductive carbon and Ag/AgCl inks were printed onto a thermoplastic polyurethane (TPU) film. The film was heat laminated over the wound dressing and then covered by a protective encapsulation layer. The active area of the fabricated electrodes was functionalized with carbon nanotubes (5 mg ml$^{-1}$) and gold nanoparticles (OD:50). The horseradish peroxidase enzyme (5 mg ml$^{-1}$) and uricase enzyme (5 mg ml$^{-1}$) were then physiosorbed over the sensor surface and air dried. The electrochemical current response of the fabricated sensors toward uric acid was determined through amperometric measurements. An increase in the reduction current corresponded directly to an increase in the uric acid (UA) level. In this exemplary embodiment the linear response range of the sensor was found to be from 0 μM to 720 μM with a correlation coefficient of 0.99 and a sensitivity of 46.77 nA μM$^{-1}$ cm$^{-2}$. The results demonstrated that the sensor can accurately measure UA in the clinically relevant range; e.g., 200-750 μM.

Example 3—Fabric Electrodes and Electronic Assembly of the Bandage

Three fabric electrodes are shown in FIG. 8. The reference electrode (RE), and working electrode (WE) are used to connect the input DC power management circuit to illuminate the sensor. The working electrode (WE) and counter electrode (CE) are used to collect the feedback voltage of the sensor to feed the VCO. An electric potential of −0.6 V was used to power the sensor using electrodes WE and RE. The feedback voltage of the sensor resulted from the uric acid detection or tuning voltage ($V_{tuning}$) is given by the electrodes CE and WE and used to feed the input of the VCO.

Example 4—Complete System and Testing

FIG. 14 illustrates the full system representing one embodiment of the subject invention. The components that are used in the electronic assembly of the system include a power management circuit used to regulate the voltage supplied by the harvesting system to supply to the electrochemical sensor as well as the VCO. The power management circuit can also be prototyped via embroidery process of conductive textiles. The resistor $R_1$ and $R_2$ are used as a power dividing system to supply the correct voltages to both the sensor and the VCO. In this example, the sensor was prototyped via the automated embroidery of conductive textiles onto fabric substrates and is used to detect the level of uric acid present in the wound. For other electrochemical sensing system embodiments, the sensor and/or additional sensors may detect the pH, temperature, oxygen level, cortisol, any combination thereof, and other chemical components useful for vital signs monitoring or sensing. The output signal obtained from the sensor is an electrical current that is combined with the resistance of $R_3$ that is used to tune the VCO. The VCO in this embodiment was also prototyped via the automated embroidery of textiles onto fabric substrates and attached to a 915-MHz textile-based patch antenna to send the wound-data wirelessly to the receiver that is represented by a Keysight PXA signal analyzer. This is one prototyping equivalent of a testing system where a proposed smart bandage embodiment of the subject invention is illuminated by a scanner (e.g., interrogator).

The system was tested as shown in FIG. 14 using a DC power supply to provide 1 V to the TI BQ25504 power management circuit that outputs 3.14 V. The latter was divided into two portions that were given to both sensor and VCO. The sensor only used 24 μW of power to operate while the VCO, 33 mW. The wound fluid was emulated using uric acid of concentrations ranging from 0 to 1 mM that were detected by the sensor. The output voltage created by the electric signal given by the sensor was found to be between 1.85 V and 2.15 V (FIG. 9(b)). The VCO modulated these signals and converted them into RF signals whose frequencies ranged from 1090 MHz to 1120 MHz (FIG. 11(d)) following the equation:

$$f_{oscillation}=1121.256+12.365\times\log_2{(0.965\times C_{UA})} \quad \text{Equation 2}$$

These signals were wirelessly transmitted to the signal analyzer using the textile-based patch antenna. The complete system was later put together and shown to be suitable to be placed on legs as shown in FIG. 10d and arm, belly, head, etc.

Example 5—Smart Wound Monitoring System

One embodiment of the subject invention is shown on FIG. 12 with a scanner (interrogator) to send an RF power signal to a textile antenna embroidered onto a band-aid or bandage, where the rectification of this signal is accomplished by a fabric-integrated rectifying circuit. The rectified power is used by an enzymatic sensor dipped in, exposed to, or in contact with the wound fluid to detect the concentration of uric acid present in the fluid. A textile-based VCO integrated to the sensor converts the electric signal according to equation (3) and modulates it into an RF frequency signal for transmission back to the interrogator device through another antenna.

$$i_{Feedback}(\mu A) = 6.234 + 0.338 \times \log_2(0.985 \times C_{UA}) \quad (3)$$

The wound severity in this embodiment is estimated by considering the uric acid level with relation to a value of, e.g., 0.4 mM, the threshold concentration above which the wound is considered severe according to Fernandez, et. al., 2012, International wound journal, vol. 9, no. 2, pp. 139-149.

Example 6—Textile-Based Electrochemical Sensor

In this representative and non-limiting embodiment, the proposed electrochemical sensor is similar to that taught by Umasankar, et. al., in 2018 IEEE SENSORS. IEEE, 2018, pp. 1-4. This sensor (FIG. 14) is comprised of three electrodes, referred to as working electrode (WE), counter electrode (CE), and reference electrode (RE) used to connect the input and output of the sensor when it is dipped in the wound fluid consisting of uric acid. WE and RE are used to power the sensor with a potential of Ev=−0.6 V as suggested in Umasankar, et. al., 2018. To measure the output current of the sensor, the WE and CE are used and connected to a resistor R=350 kΩ (see FIG. 14) placed across them and the resulting voltage is applied to the VCO to transform the wound-data, which is the DC voltage level found across the 350 kΩ-resistor, into an oscillating frequency.

Example 7—Textile-Based VCO

One aspect of the subject invention provides a textile VCO (FIG. 13(inset)) fabricated with conductive textiles embroidered onto gauze fabric, a Crystek CVCO055BE IC and two capacitors C1 and C2 with values of 1 nF and 10 nF, respectively. In this exemplary embodiment VCO was characterized for input voltages ranging from 0 to 6 V emulating the sensor feedback response and demonstrated a frequency modulation between 830 MHz and 1700 MHz over a voltage input range from about 0V to about 6V, as shown in FIG. 13.

Example 8—System Integration and Testing

In one embodiment of the subject invention, the system is tested as displayed schematically in in FIG. 14. A Keysight E36312A power supply was used to deliver power to a TI BQ25504 power management circuit (PMC) to stabilize the power required by the sensor. In addition to the PMC this embodiment contains the sensor, the VCO, and a pair of patch antennas operating at 915 MHz positioned 25 cm away, used for power reflection back to the interrogator, Keysight PXA signal analyzer (FIG. 14). It was found that for concentration of uric acid that ranged from 0.2 mM to 1 mM, the feedback voltage from the output of the VCO ranged from 1.875 V to 2.15 V (FIG. 15), which after RF modulation of the VCO was converted into frequency ranging from 1089 MHz to 1120 MHz (FIG. 15). For rapid wound healing assessment, a theoretical model of the frequency modulation was developed and is displayed in inset to the corresponding plot (FIGS. 13 and 15 (inset)). In certain embodiments, this or a similar expression may be used as calibration for the wound status in practical settings.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. An electronic system for remote sensing and monitoring of wound healing in a wound having an associated wound fluid, the electronic system comprising:
   a first textile antenna configured to receive an RF power signal;
   a fabric integrated rectifying circuit configured to convert the RF power signal to a rectified DC supply voltage, the electronic system being configured to operate normally without a power source;
   a textile based electrochemical sensor configured to receive power from the rectified DC supply voltage and output an electric signal in response to one or more wound health data values of the associated wound fluid;
   a textile based voltage controlled oscillator (VCO) configured to receive power from the rectified DC supply voltage and modulate the electric signal output by the textile based electrochemical sensor into an RF frequency signal; and
   a second textile antenna configured to transmit the RF frequency signal modulated by the textile based VCO.

2. The electronic system according to claim 1, the textile based electrochemical sensor being an enzymatic biosensor configured to monitor levels of uric acid (UA) in the associated wound fluid.

3. The electronic system according to claim 2, the enzymatic biosensor comprising a working electrode (WE), a counter electrode (CE), and a reference electrode (RE).

4. The electronic system according to claim 3, the WE and the RE being used to power the enzymatic biosensor with a sensor potential of from −0.3 V to −0.9 V from the fabric integrated rectifying circuit.

5. The electronic system according to claim 4, the sensor potential being about −0.6 V.

6. The electronic system according to claim 4, the WE and the CE being connected to a sensor output resistor having a resistance value of from 200 kΩ to 500 kΩ, and the textile based VCO being configured to read the DC voltage across the sensor output resistor.

7. The electronic system according to claim 6, the resistance value of the sensor output resistor being about 350 kΩ.

8. The electronic system according to claim 1, further comprising an interrogator and a back-end system, the interrogator configured to supply the RF power signal, receive the RF frequency signal, and relay the RF frequency signal to the back-end system for processing and data analysis.

9. The electronic system according to claim 1, the textile based VCO being configured to receive an input voltage in a range of from 0 V to 6 V and to provide an output frequency modulation at an output frequency of from 830 MHz to 1700 MHz.

10. The electronic system according to claim 1, the textile based electrochemical sensor and the textile based VCO each being configured to receive power only from the RF power signal through the fabric integrated rectifying circuit.

11. A method of monitoring wound health, the method comprising:
- providing an electronic system for remote sensing and monitoring of wound healing in a wound having an associated wound fluid, the electronic system comprising:
  - a first textile antenna configured to receive an RF power signal;
  - a fabric integrated rectifying circuit configured to convert the RF power signal to a rectified DC supply voltage, the electronic system being configured to operate normally without a power source;
  - a textile based electrochemical sensor configured to receive power from the rectified DC supply voltage and output an electric signal in response to one or more wound health data values of the associated wound fluid;
  - a textile based voltage controlled oscillator (VCO) configured to receive power from the rectified DC supply voltage and modulate the electric signal output by the textile based electrochemical sensor into an RF frequency signal; and
  - a second textile antenna configured to transmit the RF frequency signal modulated by the textile based VCO;
- applying the electronic system to a wound site in a patient, the wound site having an associated wound fluid;
- powering the electronic system with the RF power signal;
- receiving the RF frequency signal from the electronic system; and
- determining a measured wound health data value based on the RF frequency signal.

12. The method according to claim 11, further comprising:
- providing an interrogator;
- generating the RF power signal through the interrogator without contacting the electronic system;
- receiving the RF frequency signal into the interrogator without contacting the electronic system; and
- obtaining from the interrogator an output corresponding to the measured wound health data value based on the RF frequency signal, the output being an auditory response, a visual response, or a haptic response.

13. The method according to claim 11, the measured wound health data value being selected from pH of the wound, temperature of the wound, oxygenation of the wound, moisture of the wound, enzyme concentration of the wound, and uric acid concentration of the wound fluid.

14. The method according to claim 13, the measured wound health data value being uric acid concentration of the wound fluid.

15. The method according to claim 12, further comprising:
- making a wound healing assessment based on the interrogator output.

16. The method according to claim 15, the wound healing assessment being made by a healthcare professional in a formal healthcare environment.

17. The method according to claim 15, the wound healing assessment being made by a healthcare professional, caregiver, or patient in a remote setting away from a formal healthcare environment.

18. The method according to claim 11, the step of applying the electronic system to a wound site in a patient comprising applying the electronic system as part of a bandage, a dressing, or a covering conforming to a surface of the patient at or adjacent to the wound site.

19. The method according to claim 18, further comprising:
- instructing the patient to wear the electronic system as long as the bandage, the dressing, or the covering is worn.

20. An electronic system for remote sensing and monitoring of wound healing in a wound having an associated wound fluid, the electronic system comprising:
- a first textile antenna configured to receive an RF power signal;
- a fabric integrated rectifying circuit configured to convert the RF power signal to a rectified DC supply voltage, the electronic system being configured to operate normally without a power source;
- a textile based electrochemical sensor configured to receive power from the rectified DC supply voltage and output an electric signal in response to one or more wound health data values of the associated wound fluid;
- a textile based voltage controlled oscillator (VCO) configured to receive power from the rectified DC supply voltage and modulate the electric signal output by the textile based electrochemical sensor into an RF frequency signal; and
- a second textile antenna configured to transmit the RF frequency signal modulated by the textile based VCO,
- the textile based electrochemical sensor being an enzymatic biosensor configured to monitor levels of uric acid (UA) in the associated wound fluid,
- the enzymatic biosensor comprising a working electrode (WE), a counter electrode (CE), and a reference electrode (RE),
- the WE and the RE being used to power the enzymatic biosensor with a sensor potential from the fabric integrated rectifying circuit,
- the WE and the CE being connected to a sensor output resistor,
- the textile based VCO being configured to read the DC voltage across the sensor output resistor,
- the electronic system further comprising an interrogator and a back-end system, the interrogator configured to supply the RF power signal, receive the RF frequency signal, and relay the RF frequency signal to the back-end system for processing and data analysis,
- the textile based VCO being configured to receive an input voltage in a range of from 0 V to 6 V and to provide an output frequency modulation at an output frequency of from 830 MHz to 1700 MHz, and
- the textile based electrochemical sensor and the textile based VCO each being configured to receive power only from the RF power signal through the fabric integrated rectifying circuit.

\* \* \* \* \*